US008683882B2

(12) United States Patent
Jackson

(10) Patent No.: US 8,683,882 B2
(45) Date of Patent: Apr. 1, 2014

(54) APPARATUS FOR ULTRASONIC TRANSDUCER OR OTHER CONTACT SENSOR PLACEMENT AGAINST A TEST MATERIAL

(75) Inventor: Todd Jackson, Walworth, NY (US)

(73) Assignee: Ascent Ventures, LLC, Pittsford, NY (US)

( * ) Notice: Subject to any disclaimer, the term of this patent is extended or adjusted under 35 U.S.C. 154(b) by 188 days.

(21) Appl. No.: 13/241,989

(22) Filed: Sep. 23, 2011

(65) Prior Publication Data
US 2013/0074601 A1    Mar. 28, 2013

(51) Int. Cl.
G01N 9/24         (2006.01)
G01D 21/00        (2006.01)

(52) U.S. Cl.
USPC ............................. 73/866.5; 73/633; 73/634

(58) Field of Classification Search
USPC ............ 73/104, 865.7, 866.5, 632, 633, 634, 73/649, 661
See application file for complete search history.

(56) References Cited

U.S. PATENT DOCUMENTS

| | | | |
|---|---|---|---|
| 3,109,155 A * | 10/1963 | Degen | 367/87 |
| 3,448,911 A | 6/1969 | Cushman | |
| 3,574,923 A | 4/1971 | Cushman | |
| 4,211,949 A | 7/1980 | Brisken et al. | |
| 4,387,720 A * | 6/1983 | Miller | 600/472 |
| 4,600,228 A * | 7/1986 | Tarbuck | 294/189 |
| 4,852,416 A * | 8/1989 | Boone et al. | 73/866.5 |
| 4,875,614 A | 10/1989 | Cipolla et al. | |
| 4,934,671 A | 6/1990 | Laninga et al. | |
| 5,050,436 A * | 9/1991 | Kunii et al. | 73/644 |
| 5,127,573 A | 7/1992 | Chang et al. | |
| 5,576,492 A * | 11/1996 | Phalin | 73/634 |
| 5,737,963 A * | 4/1998 | Eckert et al. | 73/290 V |
| 5,959,211 A * | 9/1999 | Wagner et al. | 73/634 |
| 6,019,154 A | 2/2000 | Ma et al. | |
| 6,072,312 A * | 6/2000 | Van Den Berg | 324/207.16 |
| 6,227,501 B1 * | 5/2001 | Malcolm | 248/27.3 |
| 6,626,834 B2 * | 9/2003 | Dunne et al. | 600/444 |
| 6,800,987 B2 * | 10/2004 | Toda | 310/348 |
| 7,392,720 B2 * | 7/2008 | Howarth et al. | 73/866.5 |
| 7,552,634 B2 * | 6/2009 | Huber et al. | 73/290 V |
| 7,591,182 B2 * | 9/2009 | Sato et al. | 73/649 |
| 8,102,734 B2 * | 1/2012 | Sliwa et al. | 367/140 |
| 8,191,422 B2 * | 6/2012 | Maruyama et al. | 73/634 |
| 8,196,471 B2 * | 6/2012 | Han et al. | 73/620 |
| 8,381,591 B2 * | 2/2013 | Maev et al. | 73/588 |
| 2004/0000838 A1 | 1/2004 | Toda | |
| 2007/0062290 A1 * | 3/2007 | Roh et al. | 73/634 |
| 2009/0288490 A1 * | 11/2009 | Maruyama et al. | 73/633 |

* cited by examiner

Primary Examiner — Randy W Gibson
Assistant Examiner — Natalie Huls
(74) Attorney, Agent, or Firm — Brown & Michaels, PC

(57) ABSTRACT

A spherical bearing provides a passive apparatus that enables a contact sensor that needs to self-align to the surface of a test object. In some embodiments, the contact sensor is a transducer. This self-alignment apparatus may be used in a measurement system for aligning the face of a contact transducer to the surface of a material to be measured. The spherical bearing may be dry or may be lubricated with a liquid or with pressurized air to minimize the bearing friction and enable the transducer to self-align. The upper portion of the spherical bearing is preferably attached to a spring-loaded piston. The transducer is preferably attached to the lower portion of the spherical bearing. The spring-loaded piston holds the spherical bearing portions together and centers the floating lower bearing portion after each measurement operation. A cowling preferably retains the lower bearing portion between measurements.

19 Claims, 11 Drawing Sheets

APPARATUS FOR ULTRASONIC TRANSDUCER OR OTHER CONTACT SENSOR PLACEMENT AGAINST A TEST MATERIAL

REFERENCE TO RELATED APPLICATIONS

The subject matter of this application is related to the subject matter in a co-pending application entitled "ULTRASONIC TRANSDUCER WEAR CAP", filed on the same day as the present application. The aforementioned application is hereby incorporated herein by reference.

BACKGROUND OF THE INVENTION

1. Field of the Invention

The invention pertains to the field of contact sensors. More particularly, the invention pertains to a self-aligning apparatus for a contact sensor.

2. Description of Related Art

Ultrasonic pulse-echo testing of materials requires an ultrasonic transducer to introduce an ultrasonic stimulus wave into a test material, and for reflected ultrasonic waves to be detected and analyzed. The ultrasonic stimulus waves can be either compression or shear waves. It is common for a single ultrasonic transducer to be used to both introduce the stimulus wave and to detect reflected waves. To ensure that the stimulus wave is introduced into the test material by the transducer, and that reflected waves are conducted back to the transducer, the transducer face must be placed into good physical contact with the surface of the test material. In cases where the curvature of the test material surface is not known a priori, it is common for general purpose ultrasonic transducers to possess a flat front surface.

When a general-purpose ultrasonic transducer with a flat front surface is positioned by a skilled human operator, the operator places the transducer against a test material surface and applies pressure to push the transducer's front surface against the test material surface. The operator then adjusts the transducer alignment until proper acoustic coupling between the transducer face and the test material surface is obtained. Such manual placement of a contact transducer works, because the trained operator uses skill derived from past experience in order to adjust the transducer position. In some applications, a coupling fluid, which is conventionally water, is used between the end of the transducer and the test material surface. Transducer placement by unskilled operators or by mechanical or automated mechanisms such as robots results in less reliable transducer positioning, especially on test materials with curved surfaces, because the front surface of the transducer does not automatically align to the surface of the test material. To enable reliable and repeatable ultrasonic measurements with contact transducers, it is important that the transducer alignment process be fast and repeatable, even when the transducer is placed by an unskilled operator or by a robot.

SUMMARY OF THE INVENTION

A spherical bearing provides a passive apparatus that enables a contact sensor that needs to self-align to the surface of a test object. In some embodiments, the contact sensor is a transducer. This self-alignment apparatus may be used in a measurement system for aligning the face of a contact transducer to the surface of a material to be measured. The spherical bearing may be dry or may be lubricated with a liquid or with pressurized air to minimize the bearing friction and enable the transducer to self-align. The upper portion of the spherical bearing is preferably attached to a spring-loaded piston. The transducer is preferably attached to the lower portion of the spherical bearing. The spring-loaded piston holds the spherical bearing portions together and centers the floating lower bearing portion after each measurement operation. A cowling preferably retains the lower bearing portion between measurements.

DETAILED DESCRIPTION OF THE INVENTION

Figure 1:
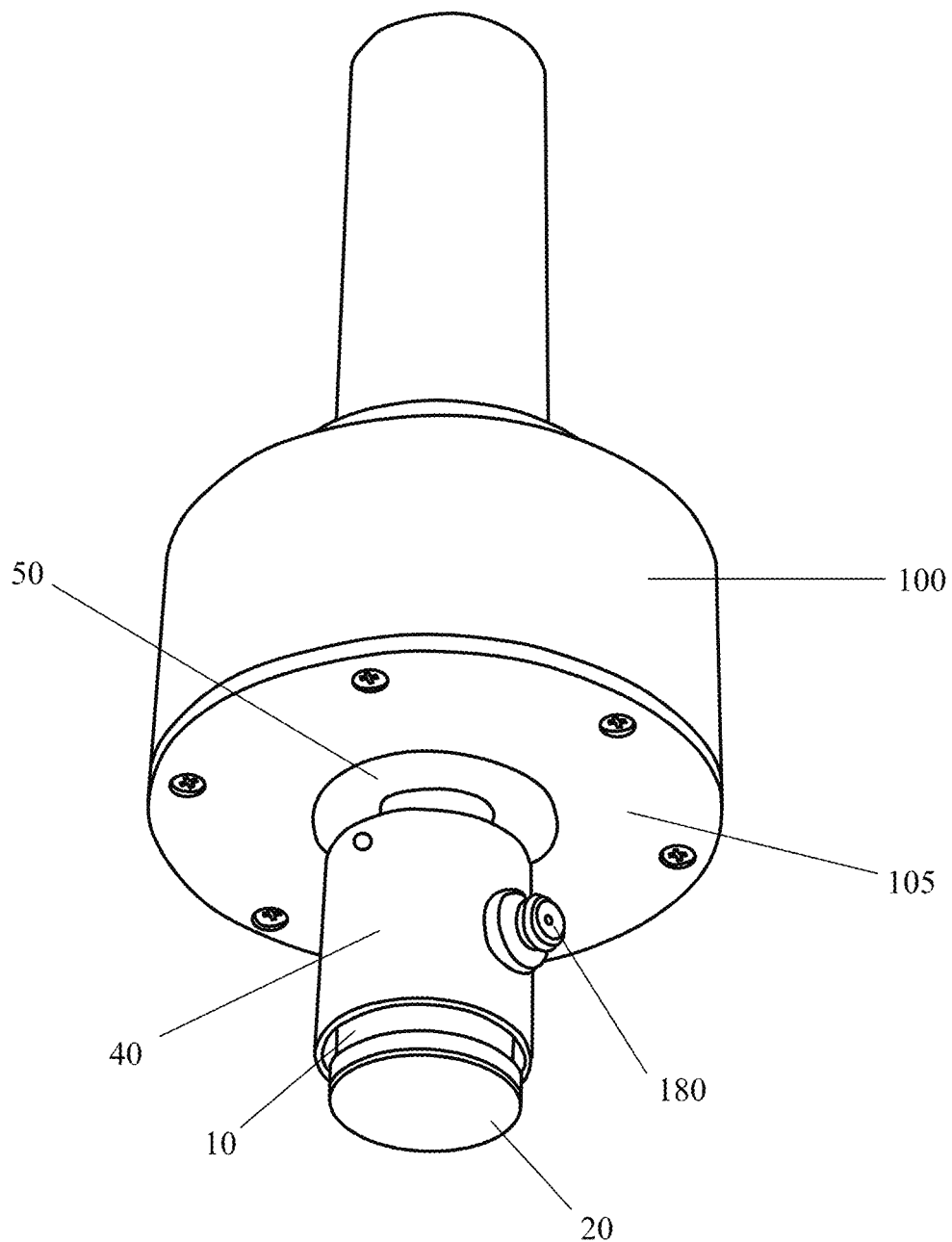
FIG. 1 shows a perspective view of a transducer with a positioning apparatus in an embodiment of the present invention.

The positioning apparatus aligns the face of a contact sensor to the surface of a material to be tested. In some embodiments, the apparatus possesses a spherical bearing and enables an ultrasonic transducer to position and self-align to a test material surface. In some embodiments, the positioning apparatus may be used for both manual and machine placement of transducers.

The positioning apparatus preferably operates passively, easily, accurately, and quickly without the need for a skilled operator or a complex machine.

The positioning apparatus preferably enables the front surface of a transducer to optimally align with flat and with curved surfaces of test materials.

The positioning apparatus preferably positions a transducer face against the surface of a test material that is immersed in air or in fluid.

The positioning apparatus preferably allows a transducer face to align to a test surface without translating laterally across the surface.

In some embodiments, the positioning apparatus is a low friction positioning apparatus based on a spherical thrust bearing that allows a transducer to pivot around a point at the center of its front surface when only a small amount of force is applied between the transducer and the test surface, thereby minimizing distortion of the test surface.

The positioning apparatus preferably achieves all the aforementioned advantages for a contact transducer possessing a replaceable protective layer or layers attached to its front surface, where the protective layers guard against damage to the transducer.

The above advantages are preferably achieved by providing a transducer positioning apparatus with a spherical bearing whose center of rotation is located at the center of the front surface of the transducer. The lower portion of the spherical bearing serves as a transducer holder and is very lightweight to minimize the effect of gravitational orientation on the transducer motion. In some embodiments, the transducer and lower bearing are self-contained and self-powered and do not require a physical electrical connection to an external device. In other embodiments, the transducer is connected to other portions of the measurement system by an electrical connection such as a thin coaxial cable. The electrical cable is preferably not springy or heavy such that the cable does not impart any torque or force to the transducer that would overcome the normalization force being generated by the face of the transducer, when it is put into contact with a test surface.

In some embodiments, pressure is applied to drive the front surface of the contact transducer into good contact with the test material surface. Any misalignment between the transducer front surface and the test material surface results in a rotational torque on the transducer, which drives the transducer toward alignment.

The spherical bearing preferably allows the transducer to rotate in response to torque so as to align its front surface to the surface of the test material. Since the spherical bearing center of rotation is located at the center of the front surface of the transducer, such rotation occurs without any translation of the transducer across the test material surface. Frictional effects of translation that would inhibit transducer alignment are thus avoided.

In some embodiments, the spherical bearing is un-lubricated. In other embodiments, the spherical bearing is lubricated using air or fluid. In yet other embodiments, the apparatus is vibrated to overcome static friction effects in the bearing. In other embodiments, a combination of lubrication and vibration is used. The effect of bearing friction that would inhibit transducer alignment is thus ameliorated. In addition, the choice of lubrication may be matched to the usage such that, for example, clean water is used as the lubricant in water-immersion applications while clean air is used as the lubricant in non-immersion applications. A flow of clean air or fluid through the spherical bearing maintains the bearing cleanliness, so the apparatus is self-cleaning in dirty environments.

In some embodiments, a coupling fluid is used between the end of the transducer and the test material surface during a test. In some embodiments, the coupling fluid is a liquid. In some embodiments, the coupling fluid is a gel. In some embodiments, the coupling fluid is water. In other embodiments, the coupling fluid is glycerin.

For a transducer possessing a replaceable protective layer or layers attached to the front surface of the transducer, the proceeding description applies with the center of the front surface of the transducer being understood to mean the point described by the projection of the center of the front surface of the transducer onto the forward-most surface of the protective layer or layers.

The apparatus preferably tolerates errors in the position and angle of a transducer placement by enabling a transducer to flatten against a curved or flat surface under gentle pressure. The test material may move relative to the apparatus and the transducer follows the test surface movement. The apparatus thus tolerates test material surface vibration well. In addition, the positioning apparatus may move relative to the test material while the transducer remains aligned with the test material. The apparatus thus tolerates well any motion of the upper part of the apparatus by the operator during or after alignment, such as hand motion resulting from manual transducer placement.

In some embodiments, the spherical thrust bearing allows an ultrasonic transducer face to pivot and flatten against the surface of a material to be tested. Preferably, the ultrasonic transducer is a type of pulse/echo layer thickness (PELT) gauge, which requires its ultrasonic transducer to be pressed into aligned contact with materials possessing coatings. More preferably, the PELT gauge is of the type produced by Imaginant, Inc. (Pittsford, N.Y.).

Typically, when a human user presses a PELT transducer against a coated surface, the transducer position may be adjusted by the user until good waveforms are produced by achieving good alignment between the transducer and the test material. However, when a robot is substituted for the human, it is difficult to achieve good results because the robot is not natively capable of adjusting the alignment of the transducer to the test material. Good results are obtained when the transducer's longitudinal axis is adjusted such that it is perpendicular to the surface of the test material.

The self-aligning mechanism is preferably a passive mechanism, rather than a computer-controlled complex device, that rapidly allows a PELT transducer to align to a test material surface so as to produce good test waveforms. Such a mechanism preferably:

1. Is simple and low-cost;
2. Functions optimally and quickly;
3. Is mechanically robust and long-lived; and
4. Requires minimal maintenance.

PELT transducers typically have a flat front surface. When pressed against a relatively flat surface, a PELT transducer has a natural tendency to align itself properly with the surface and produce good test waveforms. This is caused by the fact that two flat surfaces tend to align when pressed together. However, the transducer diameter is small and thus the alignment forces produced by pressing the transducer against the test surface are therefore weak. As a result, other small forces applied to the transducer can overwhelm the alignment forces and misalign the transducer, thereby leading to bad test waveforms.

One method for preventing undesired forces from misaligning a PELT transducer is to enable the transducer to move or pivot freely in response to normalization forces. In some embodiments, the positioning apparatus uses a spherical thrust bearing to allow the PELT transducer to align to a surface which may be flat or be of unknown curvature or topography. The axis, or center of rotation, of the spherical thrust bearing preferably coincides with the face of the transducer, and in some embodiments the spherical bearing is fluid-filled or air-filled to eliminate or substantially eliminate friction. When pressed into contact with a test surface, the spherical bearing allows the transducer to pivot and align to the test surface without interference caused by undesired forces.

A spherical bearing preferably meets all the four criteria listed above. The fact that the mechanism is passive, with the potential exception of a bearing lubricant such as compressed air, makes it very attractive for use in any application of any type of transducer, where the transducer needs to align against a surface. This may include any application outside of PELT gauges in which a transducer is maintained in contact or near contact with a surface, including, but not limited to, use of a thickness gauge based on magnetic eddy current techniques where an eddy current probe is brought into contact with a surface, underwater testing of structures such as boat hulls where it is convenient to use water as a bearing lubricant, and the testing of optical surface properties of a test material through the reflection of light off the surface of the test material from an emitter to a detector. Although in the last application the emitter and detector are not in direct contact with the surface, they may be recessed and integral to the lower bearing portion, which, by aligning itself to a test surface, causes the emitter and detector to align to the surface also.

A narrow ultrasonic beam is emitted from the center of the ultrasonic transducer face, so the center of the transducer face must be in good contact with the test surface in order for the test material to receive the ultrasonic beam. The use of a spherical thrust bearing, whose rotational point is located at the center of the face of the transducer assembly, enables the transducer assembly to normalize to both flat and curved surfaces with good contact between the center of the transducer and the surface. When the transducer is first pressed against a test material, if the point of contact is off-center, a rotational force is generated on the transducer assembly that causes the transducer to rotate, as allowed by the spherical thrust bearing, until the center of the transducer face is in contact with the test surface. Good test waveforms may then be measured.

The use of a spherical thrust bearing allows transducer alignment through rotation of the transducer about the center of the transducer's front surface. Thus, during rotation for alignment of the transducer, the transducer does not necessarily translate across the test surface. This is important because such translation may subject the transducer to frictional forces that may interfere with the alignment forces. In other words, the transducer preferably self-aligns after initial contact with the test surface without translational motion and without generation of frictional forces between the transducer and the test surface.

The use of a zero-friction spherical thrust bearing allows normalization of a transducer to occur as a result of small alignment forces. Thus, alignment can be achieved using only a small amount of force in the form of pressure to press the transducer against the test surface. The use of low force thus reduces the likelihood of the test surface to distort under applied pressure. This is very important in cases where the test surface is flexible enough that it could move to form a concavity under the face of the transducer, since this would result in a loss of contact between the center of the transducer and the test surface.

A low-friction spherical bearing may be used without lubrication, but the bearing may also be lubricated with either air or fluid to produce a very low coefficient of friction in the bearing. Lubrication thus allows the transducer to align properly in conditions that produce only small alignment forces. Many types of lubricants may be employed, but water may naturally be used as a bearing lubricant in water-immersion applications, while air may be used in non-immersive applications.

FIG. 1 illustrates a transducer 10 as used in a measurement system with a self-aligning mechanism in an embodiment of the present invention. From the perspective view of FIG. 1, the support bracket 40 for the transducer 10, the housing 100 for the self-aligning mechanism, and the lower portion 50 of the spherical bearing of the self-aligning mechanism are visible. The apparatus is generally rotationally symmetrical, and the housing 100, support bracket 40, and transducer 10 have generally cylindrical shapes. The lower portion 50 extends through a cover plate 105 affixed by fasteners to the bottom of the housing 100. A coaxial connector 180 extends from the side of the support bracket 40 to permit connection to an electricity source to power the transducer. A protective layer 20 on the face of the transducer contacts the surface to be tested and protects the end of the transducer from damage. In some embodiments, the protective layer 20 is a wear cap as shown in FIG. 1.

Figure 2:
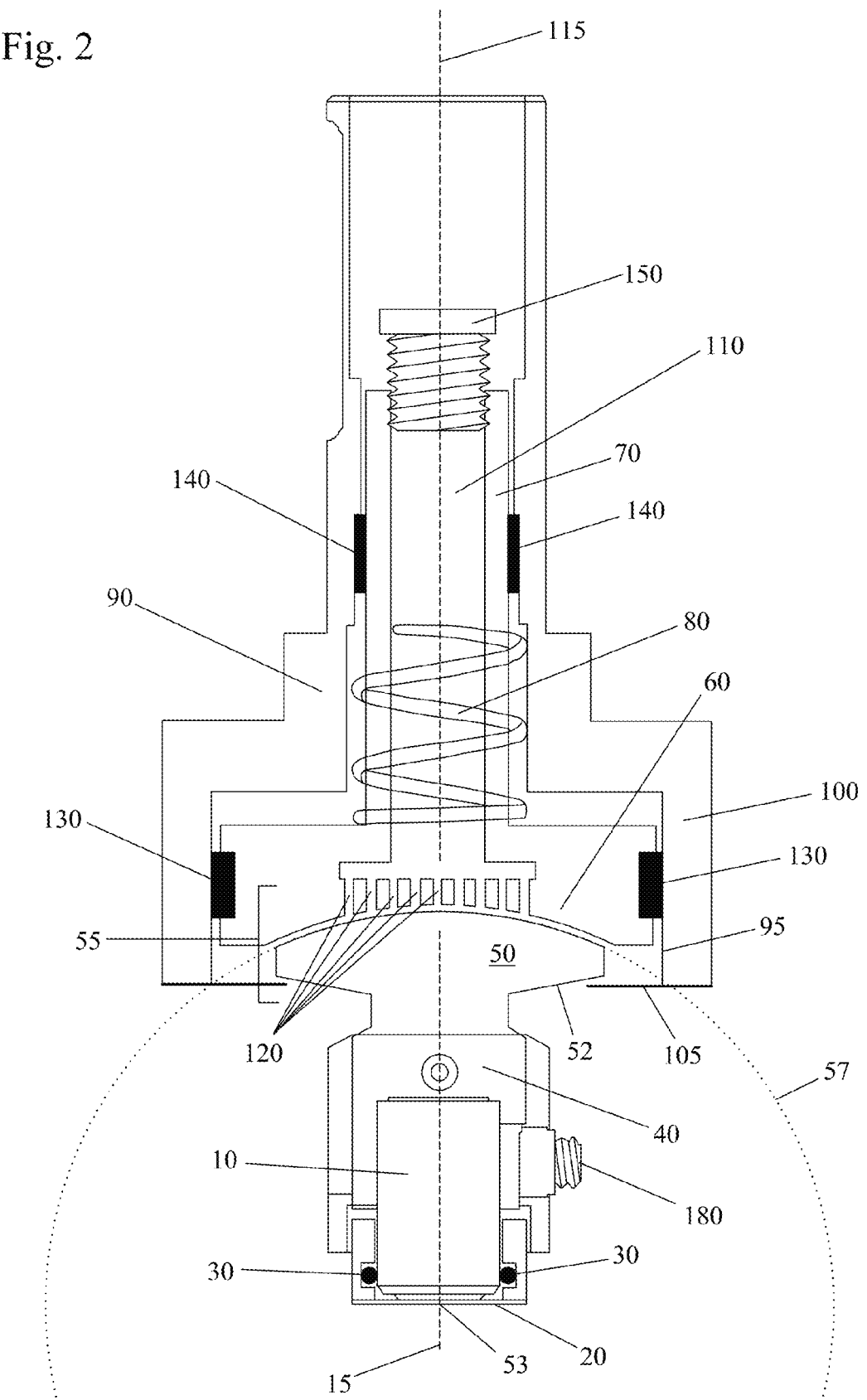
FIG. 2 shows a cross sectional view of the positioning apparatus of FIG. 1.

FIG. 2 shows that the ultrasonic transducer 10, including a protective layer 20 incorporating an O-ring 30, is securely fastened to a support bracket 40, which is made from lightweight material. The support bracket is integral to the lower portion 50 of a spherical bearing 55 such that the center of the radius of curvature of the bearing is located at the center 53 of the face of the transducer protective layer 20. The arc 57 formed with the center 53 is also shown in FIG. 2. The mating upper portion 60 of the spherical bearing 55 is coupled to or integral with a spring-loaded plunger 70 with a spring 80 that is positioned in a socket 90, which allows the spring-loaded plunger 70 to move up and down. The spherical bearing 55 is contained in a housing 100 with a cover plate 105 serving as a cowling to retain the lower spherical bearing portion 50.

The spring-loaded plunger 70, under the force of the spring 80, pushes the two bearing portions together, thereby centering the lower bearing portion 50 within the upper bearing portion 60. The shape of the back surface 52 of the lower bearing portion 50 is tapered so as to ensure that the transducer's central axis 15 properly aligns with the central axis 115 of the overall apparatus. In some embodiments, the back surface 52 of the lower bearing portion 50 is tapered and substantially conical in shape. When the apparatus is pulled away from a surface, as between the position shown in FIG. 3B and the position shown in FIG. 3C, the spring 80 forces the lower bearing portion 50 to be pressed forward against the cover plate 105. This forces the lower bearing portion 50 to align such that the central axis 15 of the transducer 10 and the upper bearing portion 60 central axis 115 become co-linear, thereby resetting the bearing assembly to be ready for the next placement against a surface. An axial passageway 110 into the spring-loaded plunger 70 connected with small channels 120 through the upper bearing portion 60 allow for the introduction of a fluid or air to the interface between the upper and lower bearing portions 50, 60 to lubricate the spherical bearing. A threaded fitting 150 allows the fluid or compressed air to be introduced into the spring-loaded plunger. Plastic bearings 130 and 140 allow the spring-loaded plunger 70 to slide without binding.

Figure 3A:
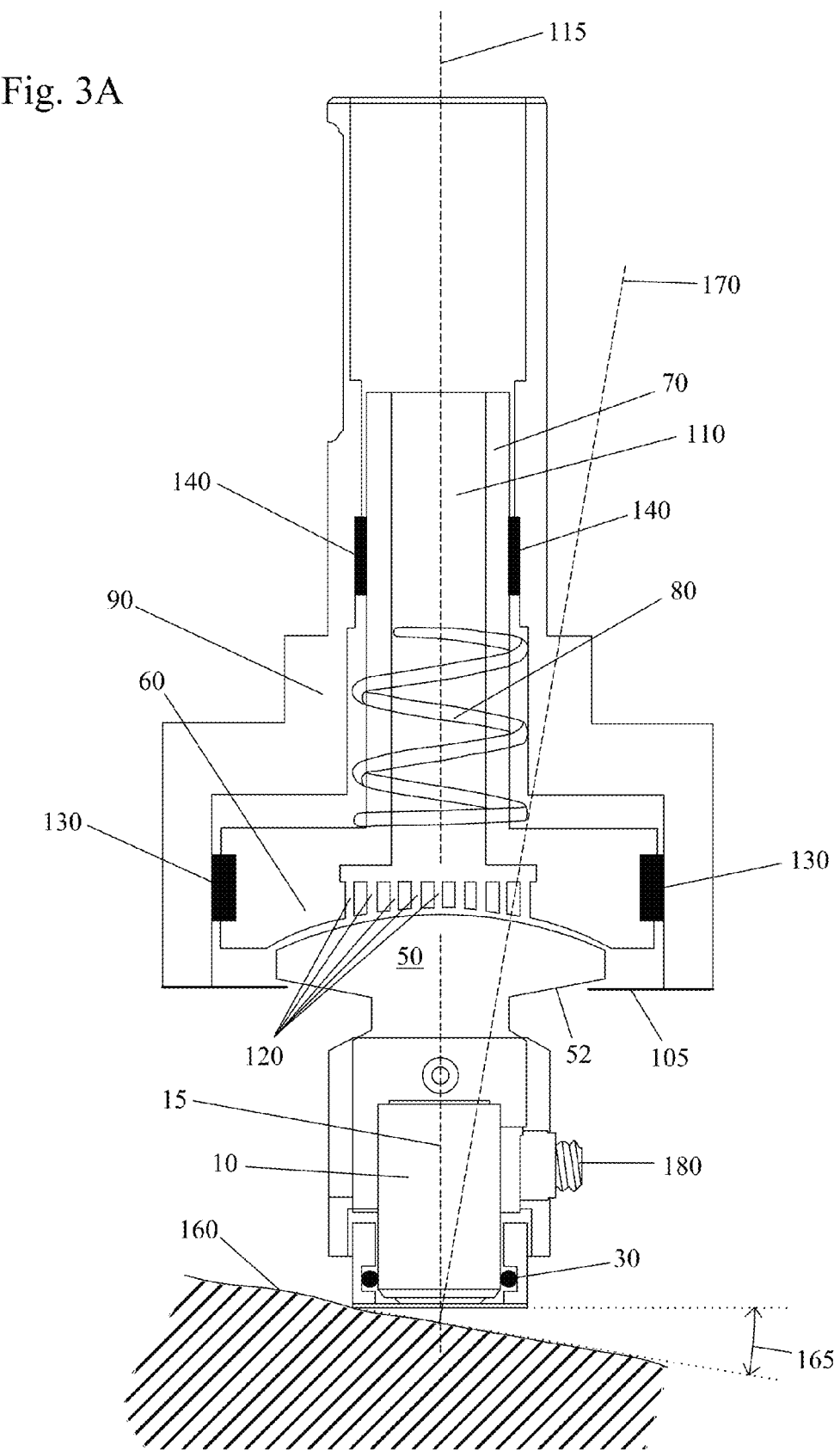
FIG. 3A shows a cross sectional view of the positioning apparatus of FIG. 1 contacting a test surface at an angle.
Figure 3B:
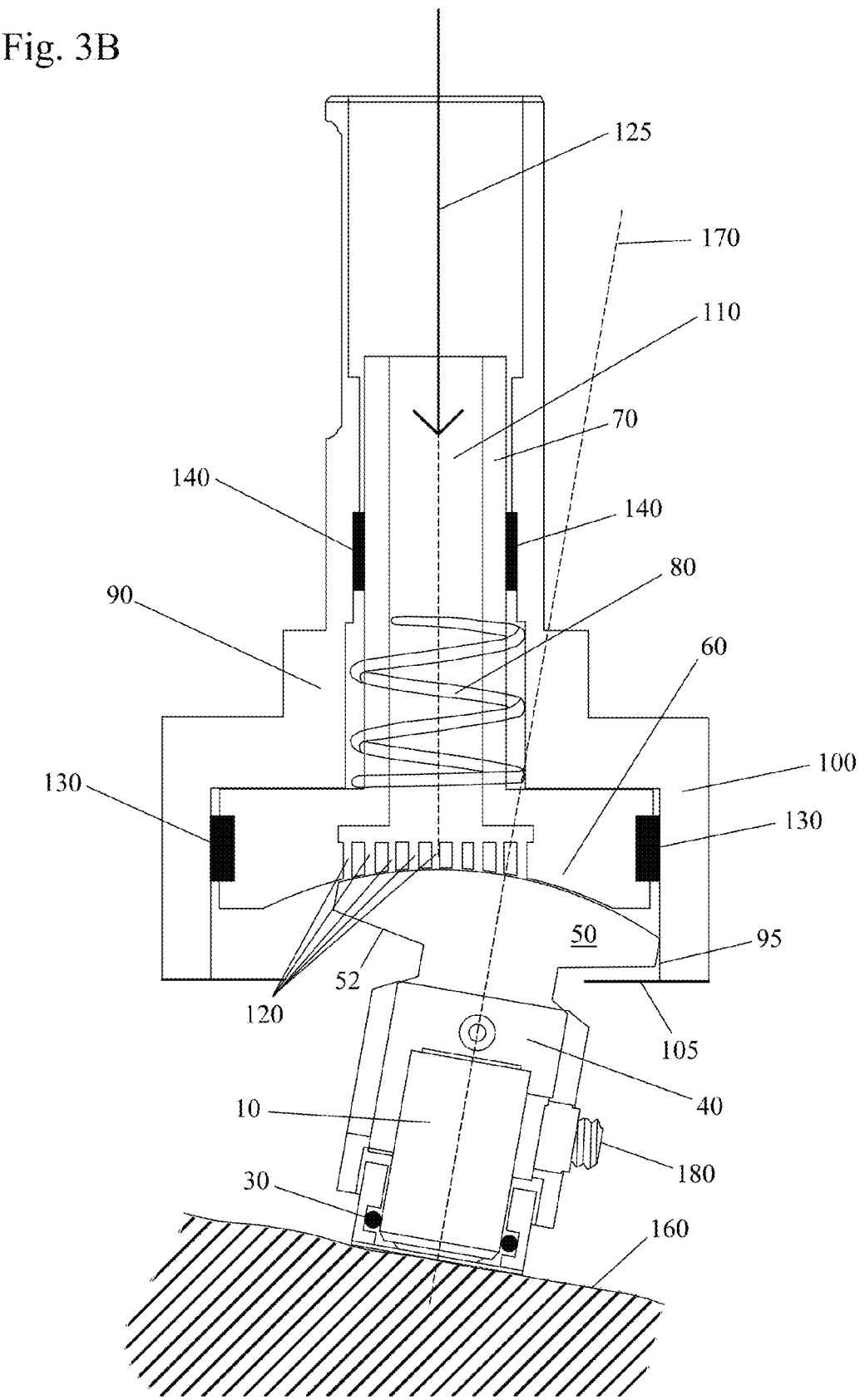
FIG. 3B shows the positioning apparatus of FIG. 3A self-aligning to the test surface.
Figure 3C:
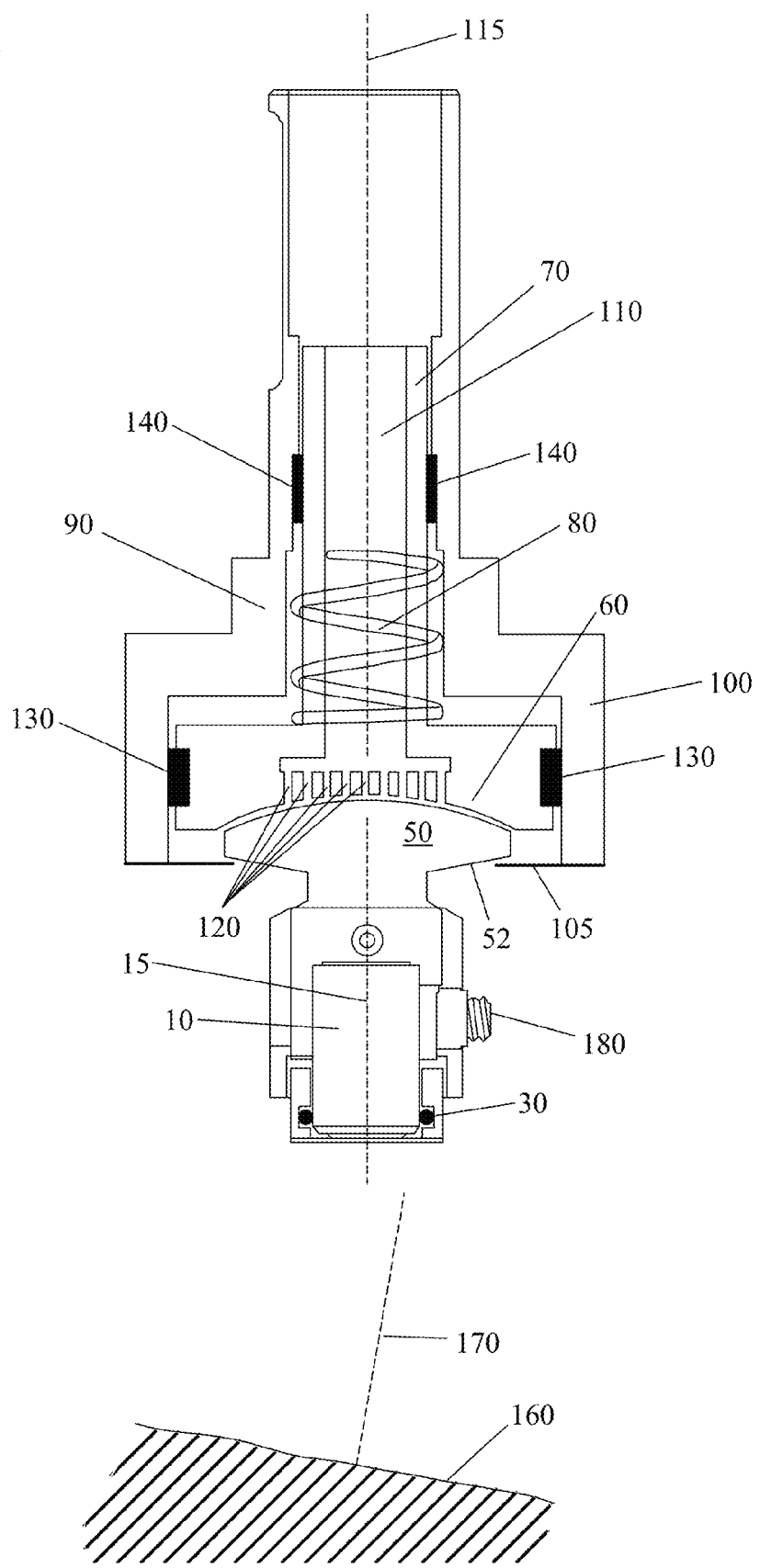
FIG. 3C shows the positioning apparatus of FIG. 3A returning to a default position after withdrawal from the test surface.

FIGS. 3A through 3C illustrate the operation of the self-aligning mechanism in an embodiment of the invention. In FIG. 3A, the apparatus is shown as it first contacts a test material surface 160 at an angle 165, which is equal to the angle formed between the central axis 15 of the transducer 10 and the line 170 normal to the surface 160 at the measurement location, resulting in a torque being applied to the transducer. The torque tends to rotate the transducer 10 in a clockwise direction from the view of FIG. 3A. As the apparatus is further pressed against the test surface 160, the left portion of the lower bearing initially pushes against the upper bearing. This pushes the upper bearing upward in the housing with the plunger 70 against the resistance of the spring 80. As the transducer 10 rotates toward alignment with the test surface 160, the lower bearing surface slides along the upper bearing surface while the lower bearing simultaneously pushes against the upper bearing, thereby retracting the plunger 70 farther and increasing the gap between the upper bearing 60 and the cover plate 105. The transducer 10 continues to rotate until the torque on the transducer is substantially eliminated when the transducer is aligned with the test surface.

In FIG. 3B, the apparatus is pictured after the spring in the spring-loaded plunger has compressed, or moved upward in the figure, thereby allowing the transducer to rotate into alignment with the test material surface and enabling a measurement to be performed. The transducer rotation may be further enabled by the lubrication of the spherical bearing with compressed air 125. In FIGS. 3A and 3B the apparatus has approached the test surface at the maximum allowable angle for the particular apparatus design. As visible in FIG. 3B, the lower bearing portion 50 has just come in contact with the side 95 of the housing 100, which prevents further rotation of the transducer. In the illustrated embodiment, this maximum angle, also denoted as angle 165 in FIG. 3A, is about 10 degrees. Since a larger maximum angle of operation requires a larger apparatus design, the apparatus design is preferably selected based on an expected maximum operable angle for the specific application for which the apparatus is to be used. Since the center of rotation is located at the front surface of the transducer, the apparatus must have a maximum angle of rotation less than 90 degrees. Preferably the maximum angle is about 45 degrees or less. For most applications, a maximum angle of about 30 degrees or less is appropriate. For many applications, a maximum angle of about 15 degrees is sufficient.

In FIG. 3C, the apparatus has been withdrawn from the test material surface and the spring-loaded plunger has realigned the spherical bearing portions in preparation for a subsequent measurement. This occurs because, upon retraction of the apparatus, the spring 80 force is no longer offset by the contact force with the test surface. The spring 80 extends to push the plunger 70 back toward the default position and reduce the gap between the upper bearing 60 and the cover plate 105, which drives the tapered edge of the lower bearing in a direction away from the gap until the lower bearing 50 is substantially re-centered on the upper bearing 60.

Figure 4:
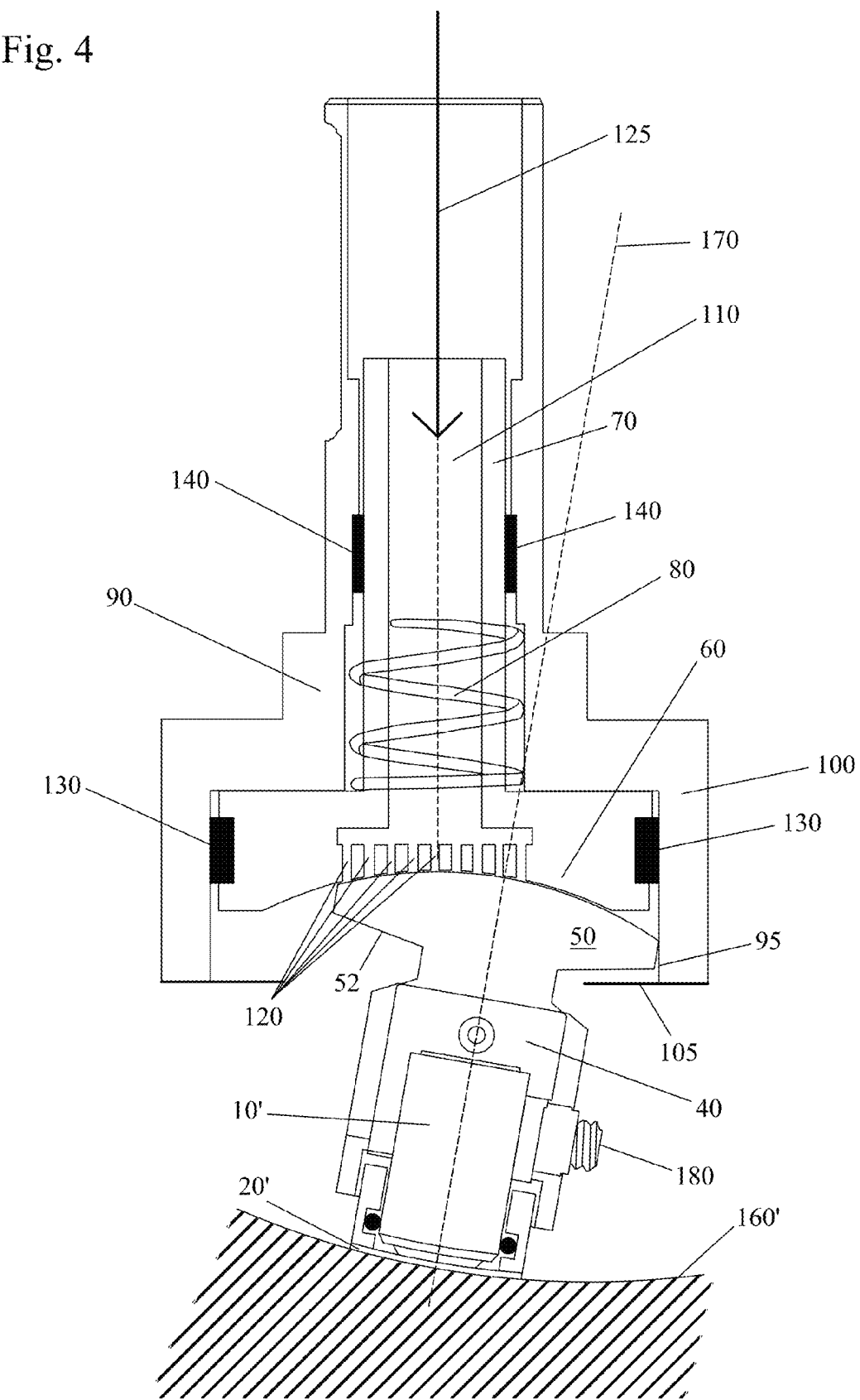
FIG. 4 shows a positioning apparatus with a curved contact surface in an embodiment of the present invention.

In the above-described embodiments, the end of the transducer 10 and the protective layer 20 are shown as being flat, but these surfaces may alternatively be curved within the spirit of the present invention. In FIG. 4, the transducer 10' and the protective layer 20' both have a curved convex shape so as to match the concave curvature of the surface 160' to which the apparatus makes contact. In such cases, the spherical bearing concept will also allow the transducer to align to the surface. Alternatively, the transducer 10' and the protective layer 20' may both have a concave shape so as to match the convex curvature of a surface 160' to which the apparatus makes contact.

In the above-described embodiments, the spherical bearing apparatus is described as being rotationally symmetric. It has been observed in some cases that during use, small forces between the transducer and measurement surfaces cause the transducer bracket to rotate slowly in one direction, on the order of a small fraction of a degree each time the apparatus makes contact with a surface, such that after many hundreds of measurements a visible rotation is observed. A small amount of rotation from a single surface contact is irrelevant, but cumulative 'rotational creep' may occur after hundreds of placements. This can cause a problem if the transducer has a physical connection, such as a coaxial cable, to an external object, because the transducer rotation may cause the cable to twist or kink. This twisting or kinking may then result in a force being applied to the transducer that may interfere with the functioning of the spherical bearing and prevent the transducer from aligning to a surface. In some embodiments the apparatus is designed to be rotationally asymmetrical in some way to cause the transducer bracket to reset to the same rotation orientation after each measurement. In some embodiments, the neck of the transducer bracket and the cover plate opening through which it passes are both complementarily slightly oval, such that in a cross section of the apparatus of FIGS. 2, 3A, 3B, and 3C along a long axis shows the back surface 52 of the lower bearing portion 50 and the cover plate 105 to be wider than a perpendicular cross section along the short axis. When the apparatus is pulled away from a surface, the spring 80 drives the plunger 70 forward against the lower bearing portion 50, which drives the back surface 52 of the lower bearing portion 50 into contact with the edges of the opening in the cover plate 105. If the opening and the back surface are both slightly oval, then the transducer bracket not only centers itself axially but also returns to its original rotational orientation as defined by the slight oval nature of the back surface and cover plate opening.

Figure 5:
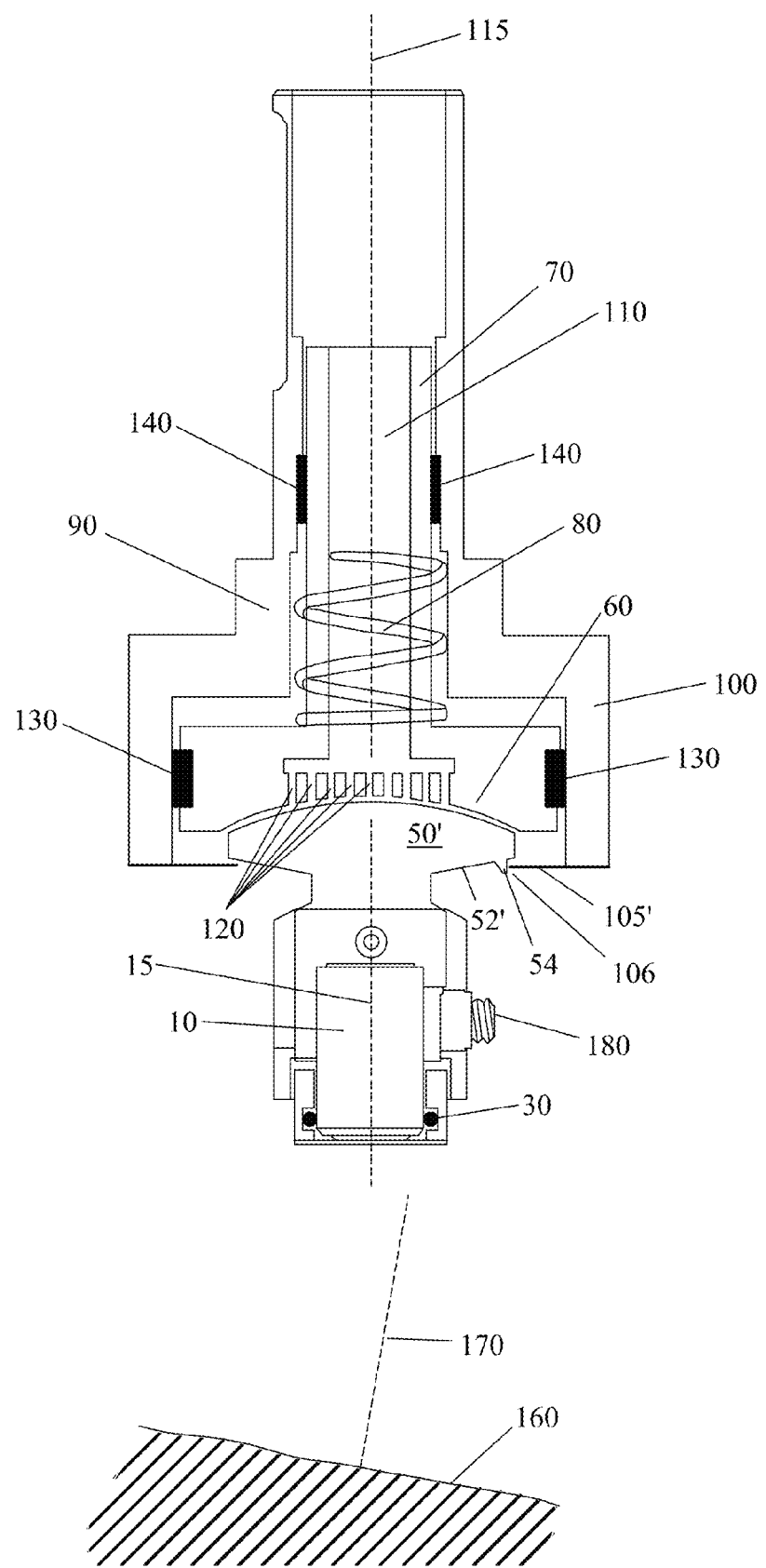
FIG. 5 shows a positioning apparatus with an alignment ridge and an alignment notch in an embodiment of the present invention.

In another embodiment, as shown in FIG. 5, a small protrusion 54 extends from the back surface 52' of the lower bearing portion 50', and a corresponding complementary recess 106 in the opening of the cover plate 105' provide rotational realignment after each placement operation. In essence, any physical feature that breaks the rotational symmetry, such that the lower bearing portion resets to a base rotational position after each placement, may be used within the spirit of the present invention. If, however, the transducer has no physical connections to external objects, then such an anti-rotation mechanism may not be required.

Preferably, a protective wear cap with a flexible barrel and rigid disc protects the front face of a high-frequency ultrasonic transducer while simultaneously maintaining good physical contact between the transducer face and the cap material. This wear cap offers utility in many ultrasonic transducer applications, including, but not limited to, high-frequency contact ultrasonic transducers used in pulse/echo layer thickness (PELT) gauges. PELT gauges require that the ultrasonic transducer and protective cap make good contact with a coated test surface such that the PELT gauge is able to make measurements of the coating thicknesses.

The wear cap rigid disc material is preferably carefully selected such that the ultrasonic signal is minimally attenuated. This is important when using high-frequency ultrasound. Although the wear cap rigid disc material and thickness are important, there are a broad range of materials that may be used for the rigid disc, both in terms of material types and in the thickness of the selected material. There is no single preferred material type for all ultrasonic transducer applications, because the best material for the wear cap varies, depending upon the item being measured. Any material may be used for a rigid disc as long as the material passes ultrasound. The material preferably has an acoustic impedance similar to the acoustic impedance of the materials being measured.

For the measurement of paint layers using PELT gauges, since paints have an acoustic impedance similar to plastic due to somewhat plastic-like physical properties, plastics are preferably used for PELT gauge wear cap rigid discs. Preferred plastics for the rigid disc include, but are not limited to, polyesters, polyetherimides, polycarbonates, polyethylenes, polymethylmethacrylates (PMMAs), polyamides, and polytetrafluoroethylenes (PTFEs). Any rigid solid plastic material may be considered for use in a wear cap rigid disc for a PELT gauge for measurement of paint thicknesses on test surfaces. Depending on the specific application, any suitable plastic, resin, or phenolic material may be used to make a wear cap material when measuring paint layers.

As an extension of the above, when measuring test materials whose acoustic impedance is significantly different from that of plastic, an optimal rigid disc material may not be plastic and may instead be a metal, glass, or ceramic material.

Placement of a high-frequency PELT transducer against a coated surface may be accomplished either by hand or by a robotic system. It is thus possible for an unprotected transducer to be damaged by rough surfaces or improper placement against a surface. A wear cap serves to protect the costly high-frequency contact transducer from physical damage resulting from contact with surfaces.

A wear cap is part of a 'sandwich'. This sandwich includes the transducer, the wear cap material, and the surface coatings to be measured. Along the path of the ultrasonic beam, any air must be eliminated in order to propagate ultrasound. Air is eliminated through the use of a coupling fluid on both sides of the wear cap which enables ultrasound to pass from the transducer into the wear cap and from the wear cap into the coating layers. At the same time, the wear cap preferably provides mechanical freedom for the transducer/wear cap and wear cap/coated surface to make good contact and to align properly such that all air is displaced by the coupling fluid and such that the reflected ultrasonic echoes are returned to the transducer. For echoes to be returned to the transducer, the transducer needs to align perpendicularly to the coated surface such that the emitted ultrasonic beam is perpendicular to the surface and thus retro-reflects back to the transducer. When a wear cap is fabricated from rigid materials, it is difficult in some situations to attain the desired alignment, which is one of the problems experienced with the use of rigid wear caps.

Figure 6:
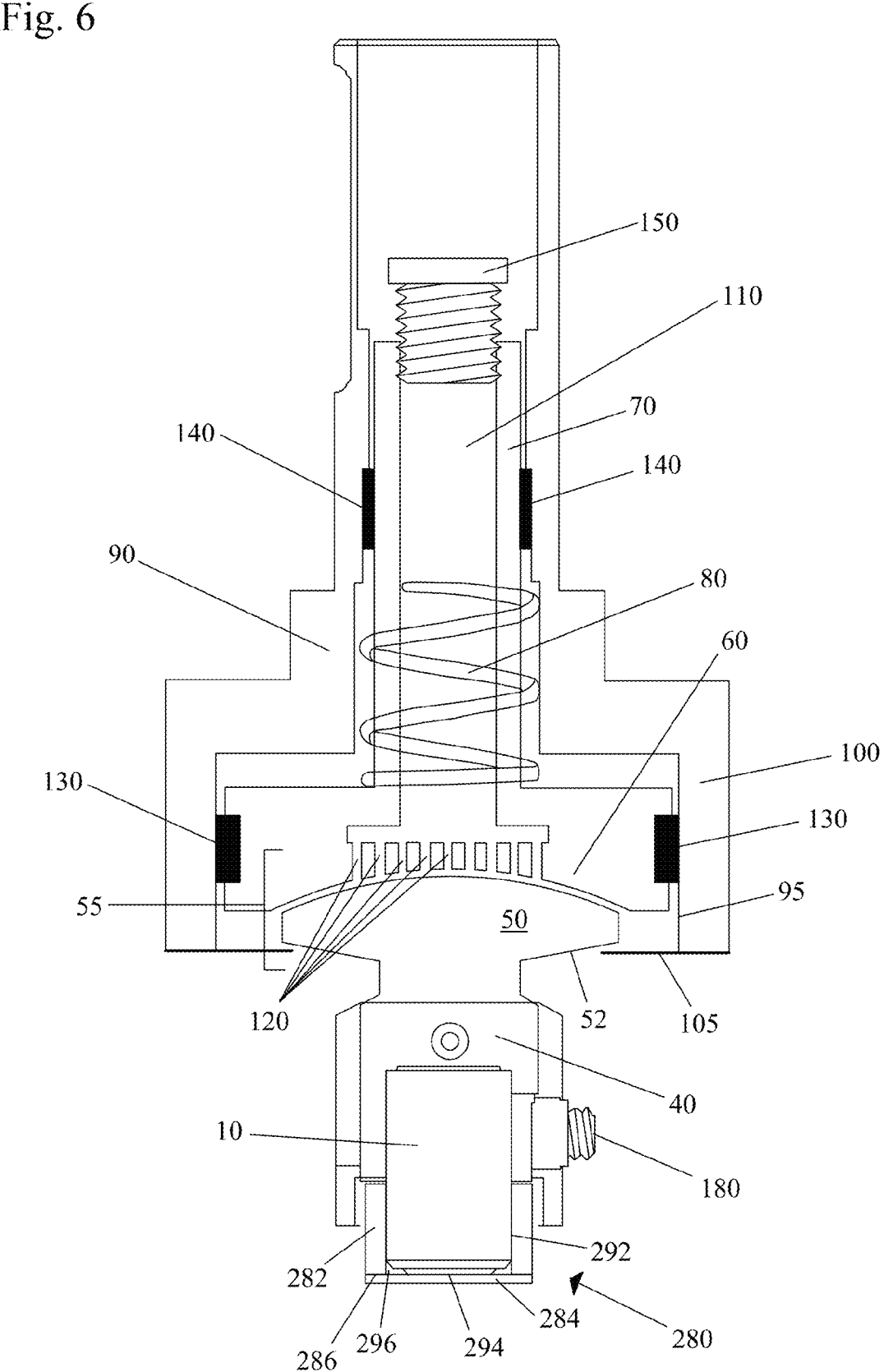
FIG. 6 shows a positioning apparatus with the ultrasonic transducer mounted in a wear cap with a flexible barrel in an embodiment of the present invention.

As shown in FIG. 6, in some embodiments of the present invention, the objectives and other advantages are achieved by affixing an end 286 of a flexible and compliant cylindrical barrel 282 to a disc of rigid material 284, thereby forming a wear cap 280 that possesses a cup shape. In some embodiments, the cylindrical barrel 282 extends above the electrical connector of the ultrasonic transducer, and a notch is formed in the wear cap 280 to receive the electrical connector. In other embodiments, the cylindrical barrel 282 is shorter than the electrical connector and does not include a notch. This wear cap 280 differs from the conventional wear cap in at least several ways. The barrel is made of a flexible material rather than a rigid material. The inner diameter of the flexible barrel is equal to or smaller than the outer diameter of the ultrasonic transducer body, rather than being larger, as in the case of conventional rigid barrel wear caps. The transducer is mounted and maintained in the flexible barrel without the use of an o-ring.

Although the specific material for the flexible barrel of the wear cap is important, there are a broad range of elastomeric materials that may be used for the flexible barrel in embodiments described herein. Materials for use in the wear cap flexible barrel include, but are not limited to, natural rubber, silicone rubber, flexible plastics, and synthetic rubbers, including, but not limited to, styrene-butadiene rubber, polybutadiene rubber, nitryl rubber, ethylene-propylene rubber, butyl rubber, polychloroprene rubber, and latex rubber.

As shown in FIG. 6, the inner diameter of the wear cap barrel 282 is preferably selected to be sufficiently small in relation to the outside diameter of an ultrasonic transducer 10 such that the wear cap barrel 282 stretches when the transducer 10 is inserted to perform multiple functions, including, but not limited to, gripping the ultrasonic transducer thereby forming a seal 292 against the ingress of dirt or contaminants, holding a small portion of ultrasonic couplant fluid in a reservoir 296 that facilitates the passage of ultrasound across any gap 294 between the transducer 10 and the wear cap disc 284, gripping the transducer 10 to retain the wear cap in its position on the transducer 10, expanding to allow trapped air or excess acoustic couplant to be expressed as the wear cap 280 is placed onto the transducer 10, and flexing to allow the wear cap front surface 284 to align with the transducer front surface and with the test material surface when gentle pressure is applied between the transducer 10 and a test material. The ultrasonic transducer preferably mounts in the wear cap without the use of any o-ring to form a seal between the wear cap and the ultrasonic transducer.

Figure 7:
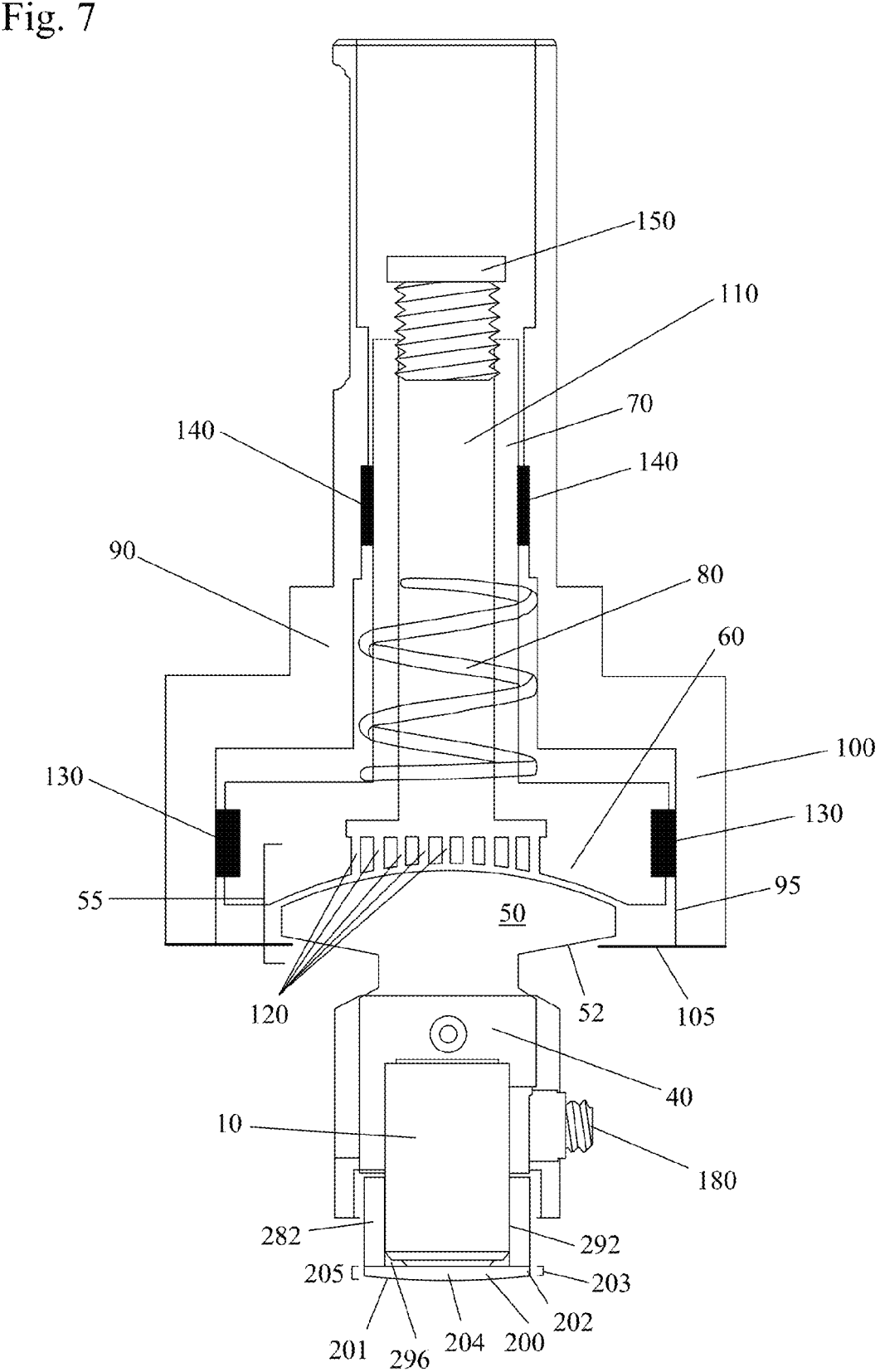
FIG. 7 shows a positioning apparatus with the ultrasonic transducer mounted in a wear cap with a curved face in an embodiment of the present invention.

Most high-frequency transducers have small-diameter ultrasonic beams whose diameter is a small fraction of the diameter of the transducer body. Thus, as an extension to the basic wear cap embodiment described herein, an alternative design employs a wear cap material with a non-uniform thickness as shown in FIG. 7. In some embodiments, the wear cap disc 200 possesses a maximum thickness 205 in the center portion 204 through which the ultrasonic beam passes but a reduced thickness 203 at its perimeter 202. The bottom surface 201 preferably has a convex shape to achieve this feature. This allows the wear cap center 204 to make good contact with both the transducer and the coated surface even when the coated surface is mildly curved. The reduced wear cap thickness 203 provides relief for the surface curvature while maintaining good contact between the transducer, wear cap, and coated surface.

Figure 8:
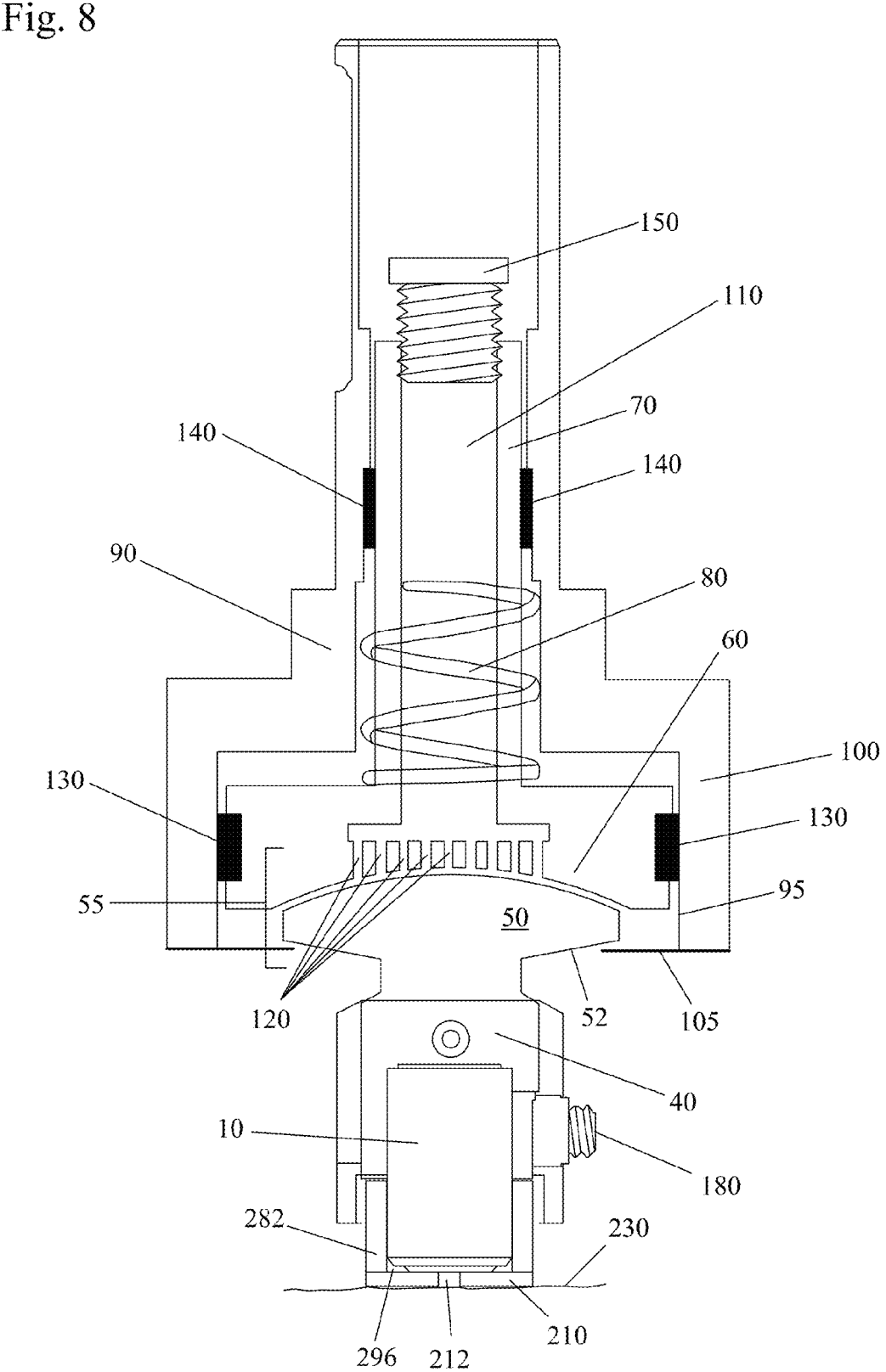
FIG. 8 shows a positioning apparatus with the ultrasonic transducer mounted in a fluid-coupled wear cap in an embodiment of the present invention.

As an extension to using a solid material for fabricating a wear cap, it is also possible to propagate ultrasound through a layer of ultrasonic coupling fluid, such as water. As shown in FIG. 8, to create a wear cap that provides the desired advantages while propagating ultrasound only through fluid, the solid wear cap includes a through-opening 212 bored through the wear cap material 210 so that no solid wear cap material remains in the path of the ultrasound. In other words, the wear cap contains an integral opening 212 through which the ultrasonic beam passes and coupling fluid may be injected to fill this opening such that the space between the transducer's front surface and the coated surface is filled with coupling fluid. Any space between the front of the transducer 10 and the coated surface 230 is preferably filled by coupling fluid. In many cases, water is used as the coupling fluid. Water has some desirable characteristics relative to the propagation of ultrasound, and water natively has the ability to eliminate any air gaps that form adjacent to surfaces. As such, the use of water or some other fluid ensures that high-frequency ultrasound is conducted to the surface 230 being tested.

The wear cap preferably retains a coupling fluid that facilitates the conduction of high-frequency ultrasound from the transducer into the wear cap material. Without such a coupling fluid, the ultrasound may be 100% reflected by a thin layer of air trapped between the transducer face and the wear cap. The wear cap thus preferably provides a reservoir 296 for the fluid.

Conventional PELT gauge products employ unfocused contact transducers for the measurement of coating thicknesses, because unfocused transducers provide thickness values that are averages of the coating thicknesses over the entire diameter of the ultrasonic beam. In contrast, in one embodiment herein, a PELT gauge employs a focused transducer. Such a gauge is advantageously able to obtain pinpoint or near-pinpoint thickness measurements rather than the average thickness measurements obtained by a conventional unfocused transducer. In this embodiment, the wear cap material properties are chosen to promote focusing of the ultrasonic beam at the surface of the coating layers of interest.

Figure 9:
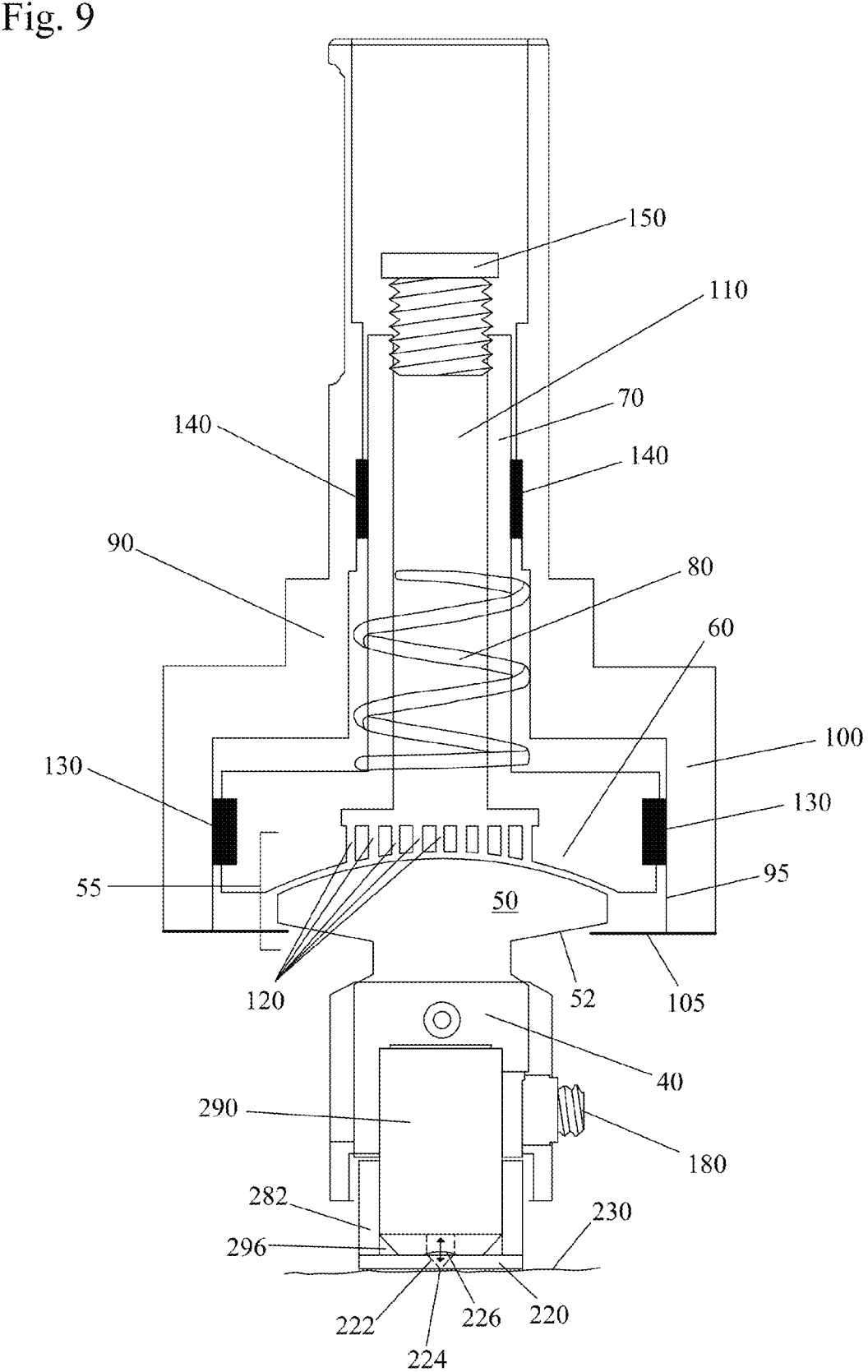
FIG. 9 shows a positioning apparatus with a focusing ultrasonic transducer mounted in a wear cap in an embodiment of the present invention.

FIG. 9 shows a wear cap that promotes focusing of the ultrasonic beam along a path 222 toward a single point 224 on the bottom surface of the wear cap disc 220. In this embodiment, the focusing is primarily a feature of the ultrasonic transducer. In other words, there is a concave lens 226 ground into the front surface of the transducer. The lens 226 on the front of the transducer 290 focuses the ultrasound at a particular distance along the path 222 of the ultrasound in 'front' of the transducer, a distance that is defined by the lens curvature and the acoustic impedance of the material in front of the transducer. In this embodiment, the beam focuses to the point 224 on the test surface 230, then 'expands' as it reflects such that it approximately follows the same conical beam line back to the transducer as it followed when emitted from the focused transducer. Thus, to ensure that the ultrasound is focused properly on the material to be measured, the wear cap preferably accomplishes two things. First, it retains an acoustic-coupling fluid in the lens cavity of the transducer so that ultrasound passes through the lens and into the wear cap, and second, the wear cap thickness is chosen such that the ultrasound focuses at the surface of the material being tested. If the thickness is too thick or too thin, the focusing is at some other (incorrect) point rather than at the surface of the material being tested. In this embodiment, the echo returns to the transducer 10 to provide a thickness value for a much smaller area of the test surface 230.

Although certain wear cap design features are shown with certain positioning apparatus designs in the figures, any of the disclosed wear cap design features may be used in combination with each other and may be used with any of the disclosed apparatus designs.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A positioning apparatus for aligning a face of a contact sensor, in contact with a test surface of a test material, normal to the test surface, the positioning apparatus comprising:
    a plunger housing having at least one bore;
    a plunger slidably received in the bore of the housing;
    a spherical bearing in the plunger housing comprising:
        an upper spherical bearing portion coupled to the plunger and having an upper spherical bearing surface; and
        a lower spherical bearing portion having a lower spherical bearing surface with a shape complementary to a shape of the upper spherical bearing surface;
    a support bracket coupled to the lower spherical bearing surface and extending from the plunger housing; and
    the contact sensor received in the support bracket;
    wherein the plunger is biased toward the lower spherical bearing portion to bias the lower spherical bearing portion toward a centered position on the upper spherical bearing portion when the positioning apparatus is not in contact with the test surface; and
    wherein a center of a radius of curvature of the lower spherical bearing surface is located on the face of the contact sensor such that the lower spherical bearing portion is rotatable with respect to the upper spherical portion about the center of the radius of curvature.

2. The positioning apparatus of claim 1, wherein an axial passageway into the plunger connected with a plurality of channels through the upper bearing portion allows for the introduction of a lubricating fluid to an interface between the upper bearing portion and the lower bearing portion in order to reduce sliding friction between the bearing surfaces.

3. The positioning apparatus of claim 2, wherein the lubricating fluid is compressed air.

4. The positioning apparatus of claim 2, wherein the lubricating fluid is water.

5. The positioning apparatus of claim 1, wherein a spring biases the plunger toward the lower spherical bearing portion.

6. The positioning apparatus of claim 1, wherein the contact sensor is a transducer for ultrasonic testing.

7. The positioning apparatus of claim 1, wherein the positioning apparatus is formed such that the lower spherical bearing portion is rotatable by an angle of up to about 10 degrees away from the centered position on the upper spherical bearing portion.

8. The positioning apparatus of claim 1, wherein the contact sensor comprises a transducer and a protective layer covering an end of the transducer, such that the protective layer forms the face of the contact sensor and contacts the test surface.

9. The positioning apparatus of claim 8, wherein the protective layer and the end of the transducer have a shape selected from the group consisting of flat, concavely curved, and convexly curved.

10. The positioning apparatus of claim 1, wherein a back surface of the lower spherical bearing portion and an opening formed by a cover plate coupled to an end of the plunger housing have complementary rotationally-asymmetric shapes.

11. The positioning apparatus of claim 1, wherein the contact sensor comprises a transducer and a wear cap covering an end of the transducer, the wear cap comprising:
    a flexible barrel having a cylindrical shape; and
    a rigid disc affixed to an end of the flexible barrel, the rigid disc forming the face of the contact sensor and contacting the test surface;
    wherein the flexible barrel has an inner diameter equal to or smaller than an outer diameter of the transducer such that the flexible barrel stretches to receive the transducer.

12. The positioning apparatus of claim 11, wherein the rigid disc has a thickness tapering from the center to the edges of the disc.

13. The positioning apparatus of claim 11, wherein the rigid disc includes a through-hole in the center of the rigid disc formed such that an ultrasonic beam from the transducer passes through the through-hole without passing through the material of the rigid disc.

14. The positioning apparatus of claim 11, wherein a thickness of the rigid disc is selected to locate a focus point of an ultrasonic beam of the transducer to coincide with a test surface.

15. The positioning apparatus of claim 11, wherein the flexible barrel is formed such that a seal is formed between the flexible barrel and the transducer without using an o-ring.

16. The positioning apparatus of claim 11, wherein the flexible barrel is made of a material selected from the group consisting of natural rubber, silicone rubber, flexible plastic, synthetic rubber, styrene-butadiene rubber, polybutadiene rubber, nitryl rubber, ethylene-propylene rubber, butyl rubber, polychloroprene rubber, and latex rubber.

17. A method of aligning a face of a contact sensor normal to a test surface of a test material, the method comprising the steps of:
    a) positioning a positioning apparatus such that the face of the contact sensor contacts the test surface, wherein the positioning apparatus comprises:
        a plunger housing having at least one bore;
        a plunger slidably received in the bore of the housing;
        a spherical bearing in the plunger housing comprising:

an upper spherical bearing portion coupled to the plunger and having an upper spherical bearing surface; and
a lower spherical bearing portion having a lower spherical bearing surface with a shape complementary to a shape of the upper spherical bearing surface;
a support bracket coupled to the lower spherical bearing surface and extending from the plunger housing; and
the contact sensor received in the support bracket;
wherein a center of a radius of curvature of the lower spherical bearing surface is located on the face of the contact sensor; and
b) applying a torque to the support bracket by positioning the plunger housing to press the face of the contact sensor against the test surface to cause the lower spherical bearing portion to rotate with respect to the upper spherical portion about the center of the radius of curvature of the lower spherical bearing surface to bring the contact sensor into alignment normal to the test surface.

18. The method of claim 17 further comprising the step of measuring a feature of the test surface using the contact sensor.

19. The method of claim 17 further comprising the step of withdrawing the positioning apparatus from contact with the test surface such that the plunger is biased toward the lower spherical bearing portion to bias the lower spherical bearing portion toward a centered position on the upper spherical bearing portion.

* * * * *